(12) United States Patent
Chalvignac

(10) Patent No.: US 8,251,062 B2
(45) Date of Patent: Aug. 28, 2012

(54) BREATHING ASSISTANCE DEVICE, AND METHOD OF REGULATION

(75) Inventor: Philippe Chalvignac, Achéres la Forêt (FR)

(73) Assignee: ResMed Paris (FR)

( * ) Notice: Subject to any disclaimer, the term of this patent is extended or adjusted under 35 U.S.C. 154(b) by 1315 days.

(21) Appl. No.: 10/553,643

(22) PCT Filed: Jan. 27, 2004

(86) PCT No.: PCT/IB2004/000898
§ 371 (c)(1),
(2), (4) Date: Oct. 14, 2005

(87) PCT Pub. No.: WO2004/067070
PCT Pub. Date: Aug. 12, 2004

(65) Prior Publication Data
US 2006/0196508 A1    Sep. 7, 2006

Related U.S. Application Data

(60) Provisional application No. 60/496,074, filed on Aug. 18, 2003.

(30) Foreign Application Priority Data

Jan. 27, 2003 (FR) ..................... 03 00858

(51) Int. Cl.
*A62B 7/04* (2006.01)
*F16K 31/26* (2006.01)

(52) U.S. Cl. ......... 128/204.26; 128/204.18; 128/204.21; 128/204.23

(58) Field of Classification Search ............. 128/204.23, 128/204.18, 204.21, 204.26, 200.24, 203.14; 415/30; 416/44–53
See application file for complete search history.

(56) References Cited

U.S. PATENT DOCUMENTS

| 5,443,061 A | * | 8/1995 | Champain et al. | ........ 128/204.21 |
| 5,740,795 A | * | 4/1998 | Brydon | ................... 128/204.21 |
| 5,803,066 A | * | 9/1998 | Rapoport et al. | ........ 128/204.23 |
| 5,927,274 A | * | 7/1999 | Servidio et al. | .......... 128/204.18 |
| 6,332,463 B1 | * | 12/2001 | Farrugia et al. | .......... 128/204.18 |
| 6,345,619 B1 | * | 2/2002 | Finn | ......................... 128/204.21 |
| 6,571,599 B1 | * | 6/2003 | Surjadi et al. | .................. 73/1.62 |

(Continued)

FOREIGN PATENT DOCUMENTS

EP    0 425 092 A1    5/1991

(Continued)

*Primary Examiner* — Justine Yu
*Assistant Examiner* — Colin W Stuart
(74) *Attorney, Agent, or Firm* — Lerner, David, Littenberg, Krumholz & Mentlik, LLP

(57) ABSTRACT

A breathing assistance device having: a turbine for generating flow of pressurized respiratory gas, a duct for carrying pressurized gas to a patient, a mechanism to control gas pressure capable of elaborating a pressure setting for the turbine, the turbine is connected to a speed sensor for acquiring a signal corresponding to the rotation speed of a rotating element of the turbine, and the mechanism of controlling the calculation linked to the speed sensor in order to elaborate using the signal, a pressure setting sending the pressure setting to the turbine. Another aspect of the invention relates to a method for regulating the pressure of a respiratory gas delivered by a turbine to a patient, the method involving elaborating a pressure setting for the turbine, characterized in that the pressure setting is elaborated using a signal representative of the rotation speed of a rotating element of the turbine.

22 Claims, 9 Drawing Sheets

100a-Turbine
110a-Duct
120a-Means for allowing a patient to receive pressurized gas
130b-Flowmeter
131b-Connection
132b-Means of calculation

U.S. PATENT DOCUMENTS

| | | | | |
|---|---|---|---|---|
| 6,626,175 B2 * | 9/2003 | Jafari et al. | ............... | 128/204.21 |
| 6,895,962 B2 * | 5/2005 | Kullik et al. | .............. | 128/204.18 |
| 2001/0004894 A1 | 6/2001 | Bourdon | | |
| 2002/0005197 A1 * | 1/2002 | DeVries et al. | .......... | 128/204.21 |
| 2003/0015200 A1 | 1/2003 | Hansen | | |

FOREIGN PATENT DOCUMENTS

| | | |
|---|---|---|
| EP | 0 505 232 A1 | 9/1992 |
| EP | 0 656 216 A2 | 6/1995 |
| WO | WO-97/10019 A1 | 3/1997 |
| WO | WO-00/66207 A1 | 11/2000 |

* cited by examiner

100a-Turbine
110a-Duct
120a-Means for allowing a patient to receive pressurized gas
130b-Flowmeter
131b-Connection
132b-Means of calculation 100a-Turbine
110a-Duct
120a-Means for allowing a patient to receive pressurized gas
131b-Connection
132b-Means of calculation
 240-Circuit
 241-First Connection
 242-Second Connection
 243-Connection
 250-Pressure Sensor

TRIGGERING OF INSPI CYCLE BY
FAST EFFORT DETECTION

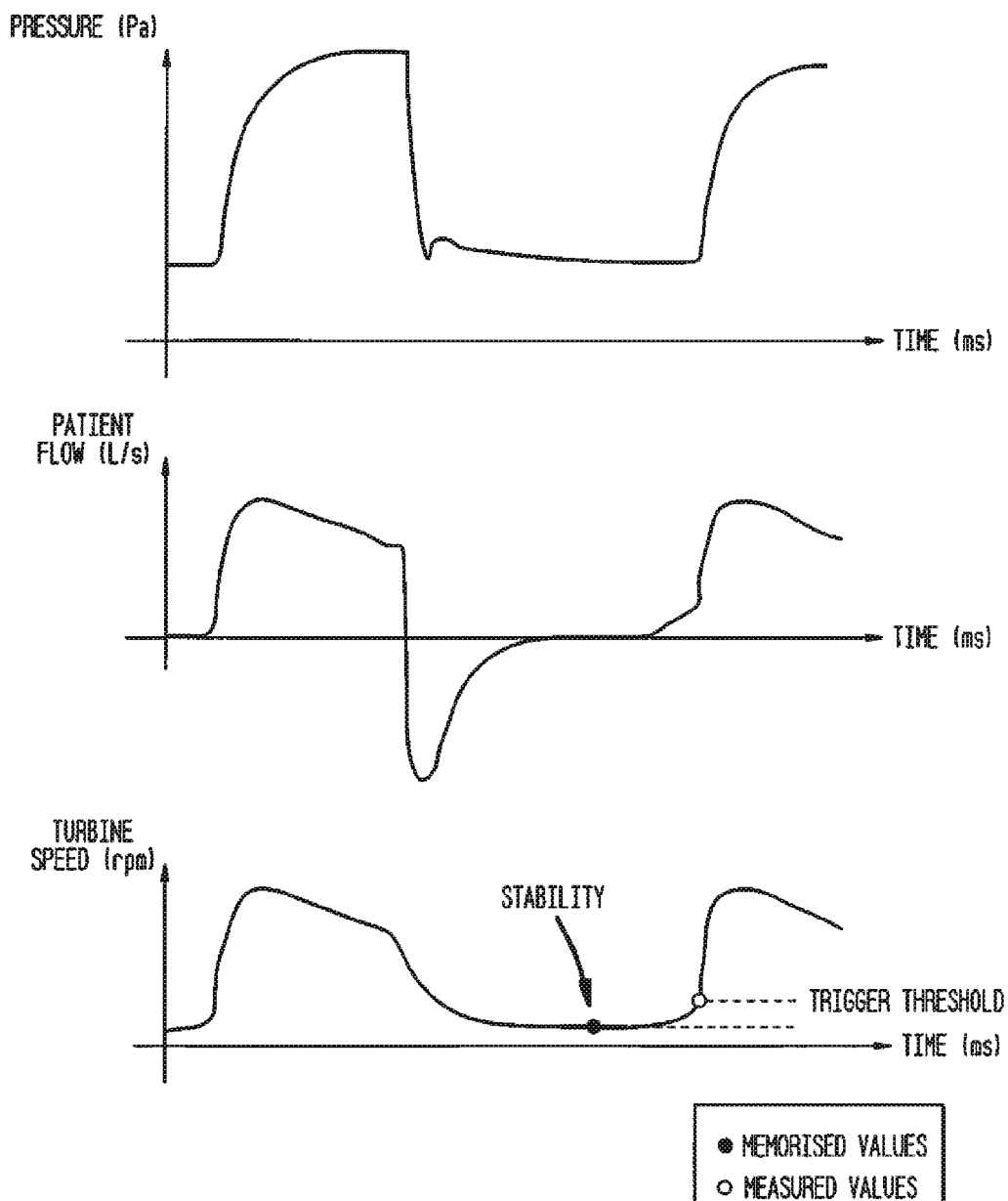

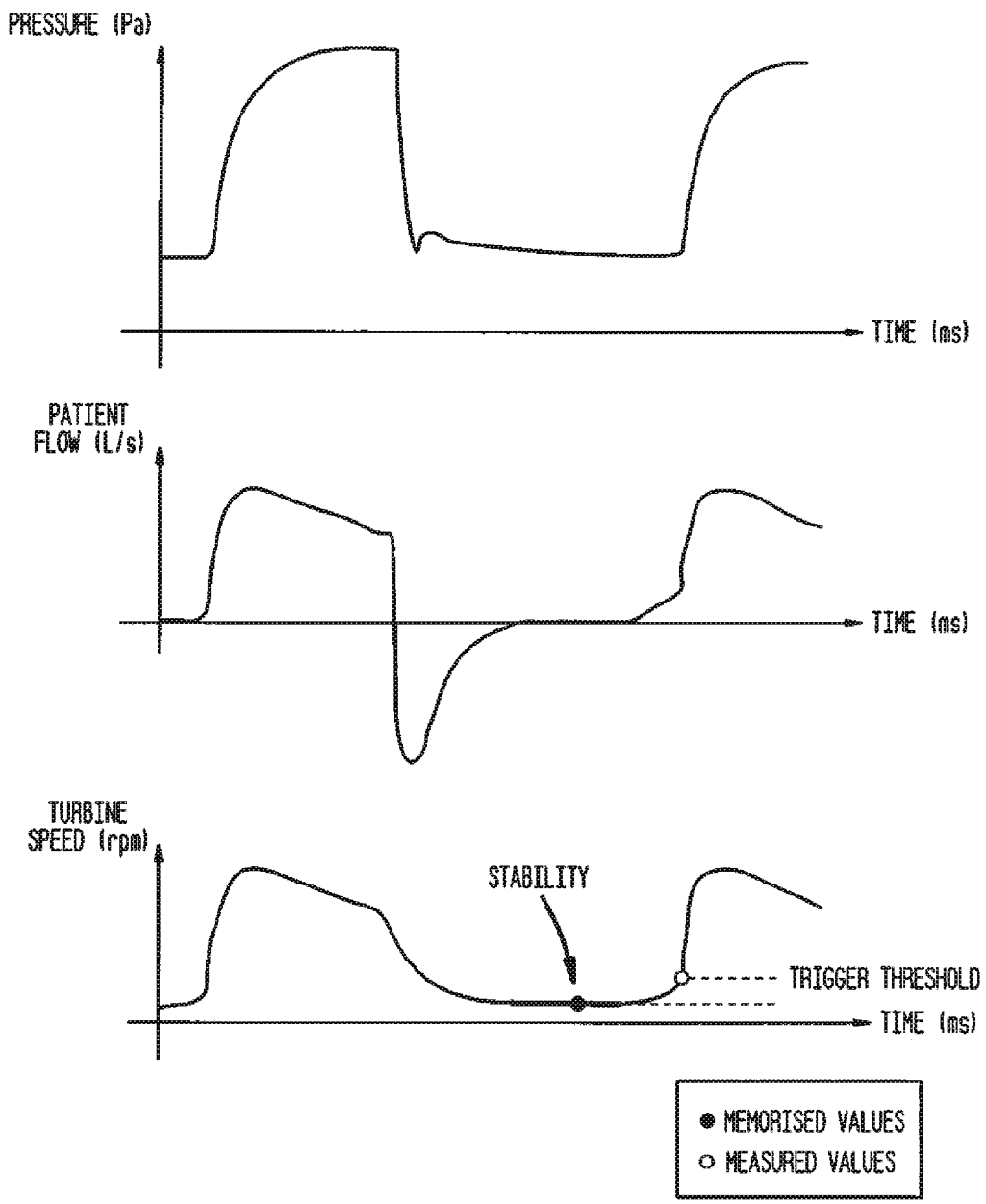

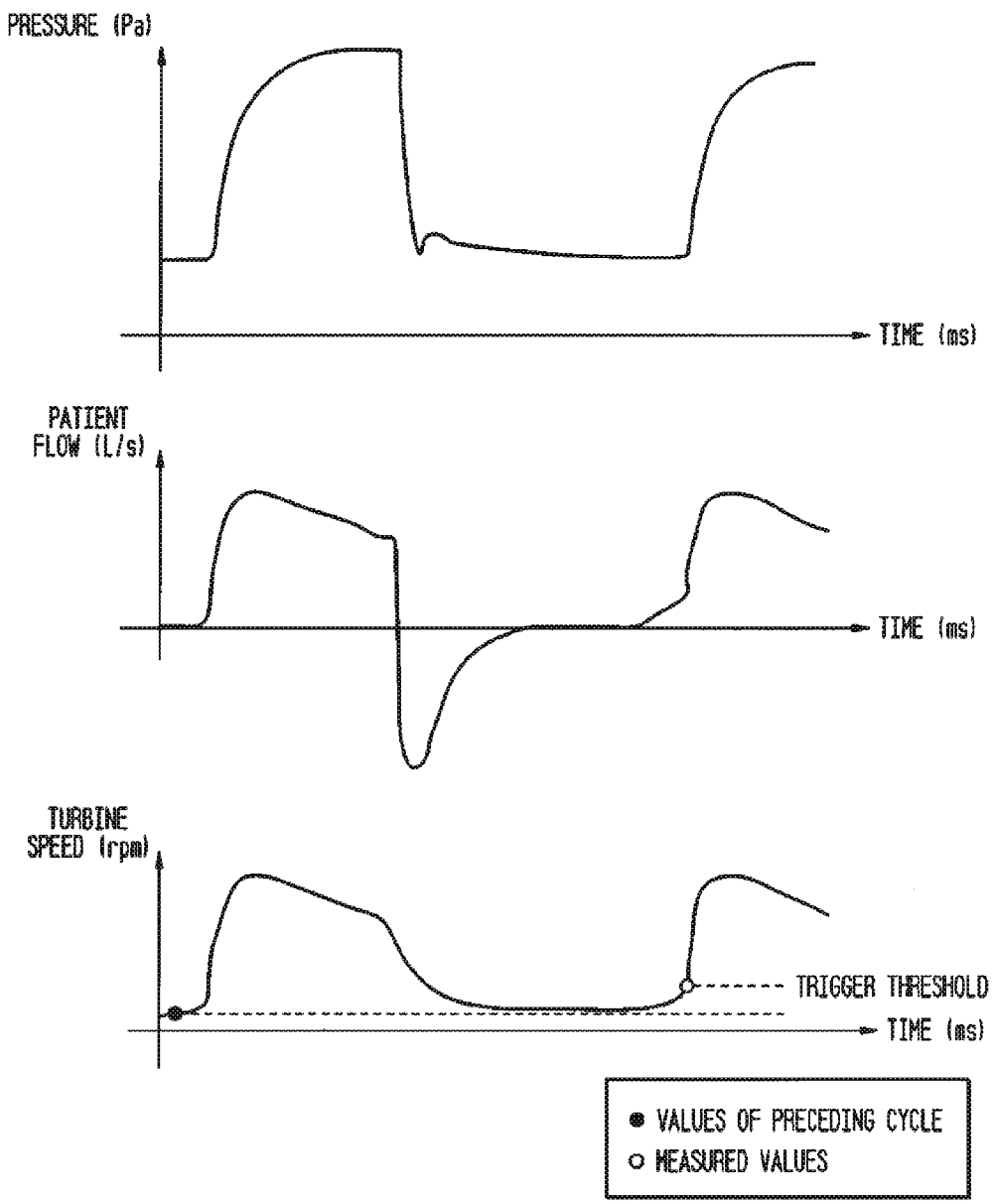

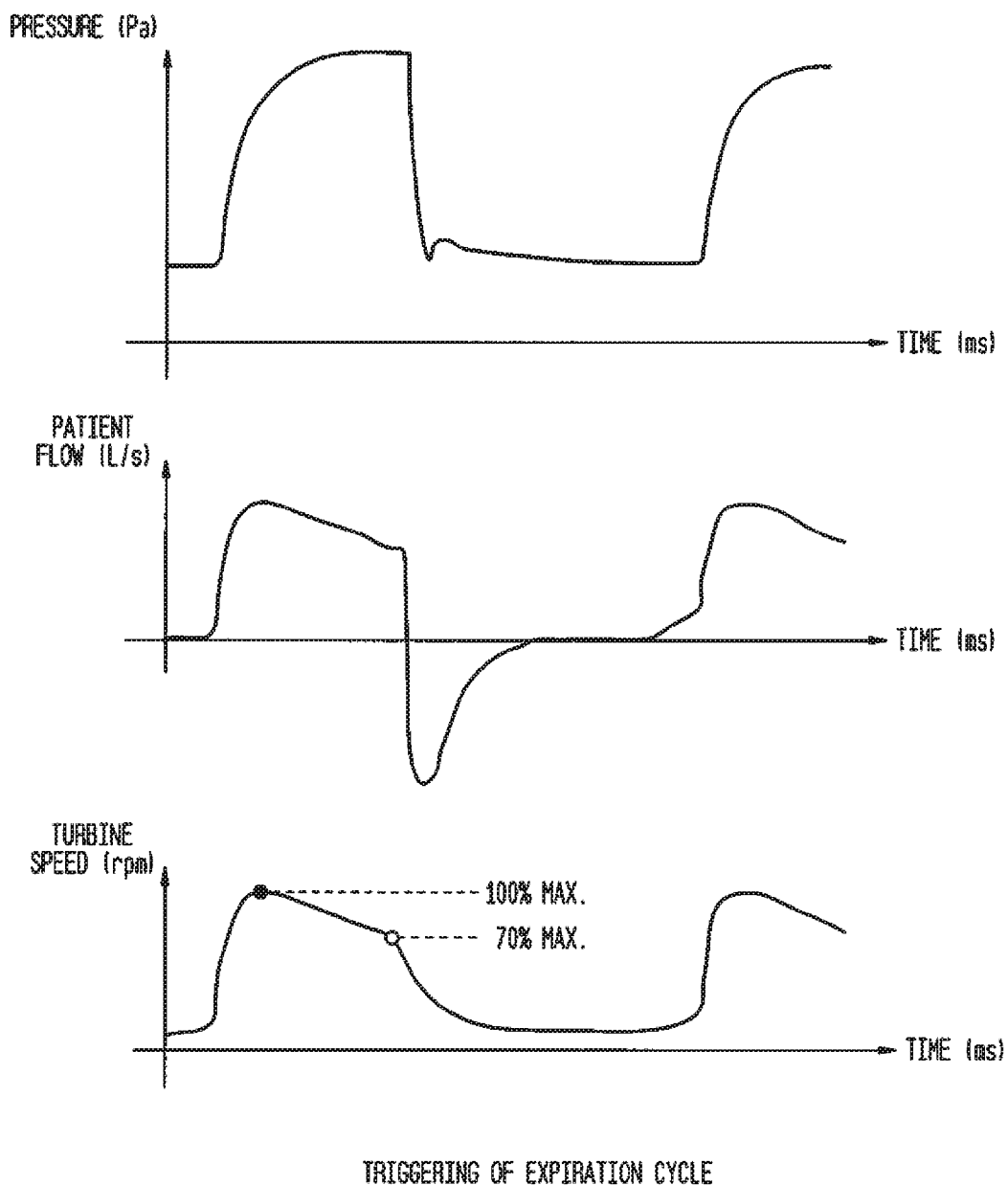

BREATHING ASSISTANCE DEVICE, AND METHOD OF REGULATION

CROSS REFERENCE TO RELATED APPLICATIONS

The present application is a U.S. national stage application of International Application No. PCT/IB2004/000898, filed on Jan. 27, 2004, which claims the benefit of French Application No. 0300858, filed on Jan. 27, 2003, and of U.S. Provisional Patent Application No. 60/496,074, filed on Aug. 18, 2003.

This invention relates in general to methods and devices for breathing assistance.

More precisely, the invention relates to a breathing assistance device comprising:
- a turbine to generate a flow of pressurised respiratory gas,
- a duct to carry the pressurised gas to a patient,
- means for controlling the gas pressure capable of elaborating a pressure setting for the turbine.

And the invention also relates to a method for regulating the pressure of a respiratory gas delivered by a turbine to a patient, the method consisting of elaborating a pressure setting for the turbine.

Devices of the type mentioned above already exist.

The basic architecture of such devices is shown in a very schematic manner in FIG. 1a, which shows a device 10a consisting of a turbine 100a allowing to generate a flow of pressurised respiratory gas (air or other), a means 120a allowing a patient to receive said pressurised gas and a duct 110a to carry the gas from the turbine 100a to means 120a.

Means 120a is generally made up of a mask that can include vents to make respiratory gas leaks possible.

Note that this means can be replaced with an expiratory valve. And the invention applies to devices with leakage masks as well as to expiratory valve devices.

Note that the term "patient" is here used broadly, and does not necessarily correspond to a person afflicted with an extensive pathology.

The devices according to the invention can thus be implemented for numerous applications, for example to provide respiratory assistance while a patient is sleeping with a view to treating sleep apnea.

However, the devices according to the invention are not in any way limited to treating sleep apnea, which is an application of the invention mentioned here by way of non-limiting example.

The invention relates to in fact as we shall see a new type of device and associated regulation, and its applications are extremely broad.

Returning to the device of the state of the art shown in FIG. 1a, such devices are known to be implemented by controlling the pressure generated by turbine 100a in such a way that this pressure has a fixed value.

Such devices are said to be of the continuous pressure airway pressure type (and are generally known under the acronym of CPAP—Trade Mark—in English).

These devices may however not be accepted by a portion of the patients, or be improperly adapted for treating certain pathologies.

More elaborate devices also exist, in which the means of controlling gas pressure are capable of elaborating several different pressure settings for the turbine.

Such devices are shown (here again in a very schematic manner) in FIG. 1b.

This figure shows a device 10b. On this figure the elements labeled as 100a, 110a and 120a are the same as those elements in FIG. 1a.

Device 10b further comprises a flowmeter 130b capable of providing to means of calculation 132b a measurement of flow in duct 110a.

Means of calculation 132b are capable of elaborating, as a function of the measured flow, a pressure setting that will be sent to the turbine (or more precisely to a turbine operation regulation circuit) via a connection 131b.

This disposition makes it possible to adapt the pressure according to the flow measured in duct 110a, with this flow being linked to the respiratory activity of the patient.

The start of inspiration or expiration of the patient can thus in particular be detected, and the pressure setting sent to the turbine can be adapted according to the cycle (inspiration or expiration) which is in progress or which is starting.

EP 425 092 shows an example of such a device.

These devices correspond to an enhancement compared to devices of the type as shown in FIG. 1a.

But they require a flowmeter to be integrated.

Such a flowmeter is an expensive element. It furthermore has a tendency to complicate the device and to increase breakdown risks of it as well as increase its cost.

The purpose of the invention is to further enhance the devices of the type mentioned at the beginning of this text, by avoiding the inconveniences and limitations exposed above.

In order to reach this purpose, the invention offers according to a first aspect a breathing assistance device comprising:
- a turbine to generate a flow of pressurised respiratory gas,
- a duct to carry the pressurised gas to a patient,
- control means for controlling the gas pressure capable of elaborating a pressure setting for the turbine,
- characterised in that the turbine is associated to a speed sensor capable of acquiring a signal corresponding to the rotation speed of a rotating element of the turbine, and the control means include means of calculation connected to said speed sensor in order to elaborate from said signal a pressure setting and send said pressure setting to the turbine.

Preferable but not limited aspects of such a device are the following:
- said speed sensor implements a Hall effect sensor,
- said speed sensor is a sensor capable of acquiring a speed signal from the turbine linked directly to the rotation speed of a rotating element of the turbine,
- the means of calculation elaborate the pressure setting according to variations in speed,
- said means of calculation are capable of detecting new inspiration or expiration cycles, and to consequently adapt the level of the pressure setting,
- said means of calculation are associated to a program for detecting inspiratory cycle using a comparison between:
  - A memorised speed value extrapolated using recent values of measured speed, and
  - An instantaneous speed actually measured,
- said means of calculation are associated to a program for detecting inspiratory cycle using a comparison between:
  - A memorised speed value as representative of a recent speed bearing, and
  - An instantaneous speed actually measured,
- said means of calculation are associated to a program for detecting inspiratory cycle using a comparison between:
  - A memorised speed value as representative of a speed at the end of an expiratory cycle, and
  - An instantaneous speed actually measured,
- said means of calculation are associated to several programs for detecting inspiratory cycle operating simultaneously, and are capable of elaborating a pressure setting corresponding to a start of inspiration as soon as one of said programs for detecting inspiratory cycle has signalled a start of inspiration, the programs(s) for detecting inspiratory cycle is (are) associated to disabling means for a determined duration following the start of a new expiratory cycle, the means of calculation are associated to a program for detecting expiratory cycle, said program for detecting expiratory cycle uses a comparison between:

A maximum speed of the turbine memorised, corresponding to a cycle of inspiration, and An instantaneous speed actually measured, said means of calculation include a microprocessor connected to the speed sensor and an input for pressure setting of the turbine, the device also includes a pressure regulation loop comprising:

a pressure sensor on the duct, and a circuit receiving the pressure setting resulting from the means of calculation as well as the pressure measured by the pressure sensor, said circuit being capable of elaborating an instantaneous setting for turbine rotation speed, said circuit being connected to an input for speed setting of the turbine.

The invention offers according to a second aspect a method for regulating the pressure of a respiratory gas delivered by a turbine to a patient, the method comprising elaborating a pressure setting for the turbine, characterised in that said pressure setting is elaborated using a signal representative of the rotation speed of a rotating element of the turbine.

Preferable but not limited aspects of such a method are the following:

said signal corresponds to the rotation speed of the rotor of the turbine, the method is capable of detecting new inspiration or expiration cycles, and to consequently adapt the level of the pressure setting, the method implements a program for detecting inspiratory cycle using a comparison between:

A memorised speed value that was extrapolated using recent values of measured speeds, and An instantaneous speed actually measured, the method implements a program for detecting inspiratory cycle using a comparison between:

A memorised speed value as representative of a recent speed bearing, and

An instantaneous speed actually measured, the method implements a program for detecting inspiratory cycle using a comparison between:

A memorised speed value as representative of a speed at the end of an expiratory cycle, and An instantaneous speed actually measured, the method implements several programs for detecting inspiratory cycle operating simultaneously, and elaborates a pressure setting corresponding to a start of inspiration as soon as one of said programs for detecting inspiratory cycle has signalled a start of inspiration, the programs(s) for detecting inspiratory cycle is (are) associated to disabling means for a determined duration following the start of a new expiratory cycle, the means of calculation are associated to a program for detecting expiratory cycle, the method implements a program for detecting expiratory cycle, said program for detecting expiratory cycle uses a comparison between:

A maximum speed of the turbine memorised, corresponding to an inspiratory cycle, and An instantaneous speed actually measured, Other aspects, purposes and advantages of the invention will appear better in the following description of the invention, made in reference to the annexed drawings on which, in addition to FIGS. 1a and 1b which have already been commented in reference to the state of the art:

Figure 4:
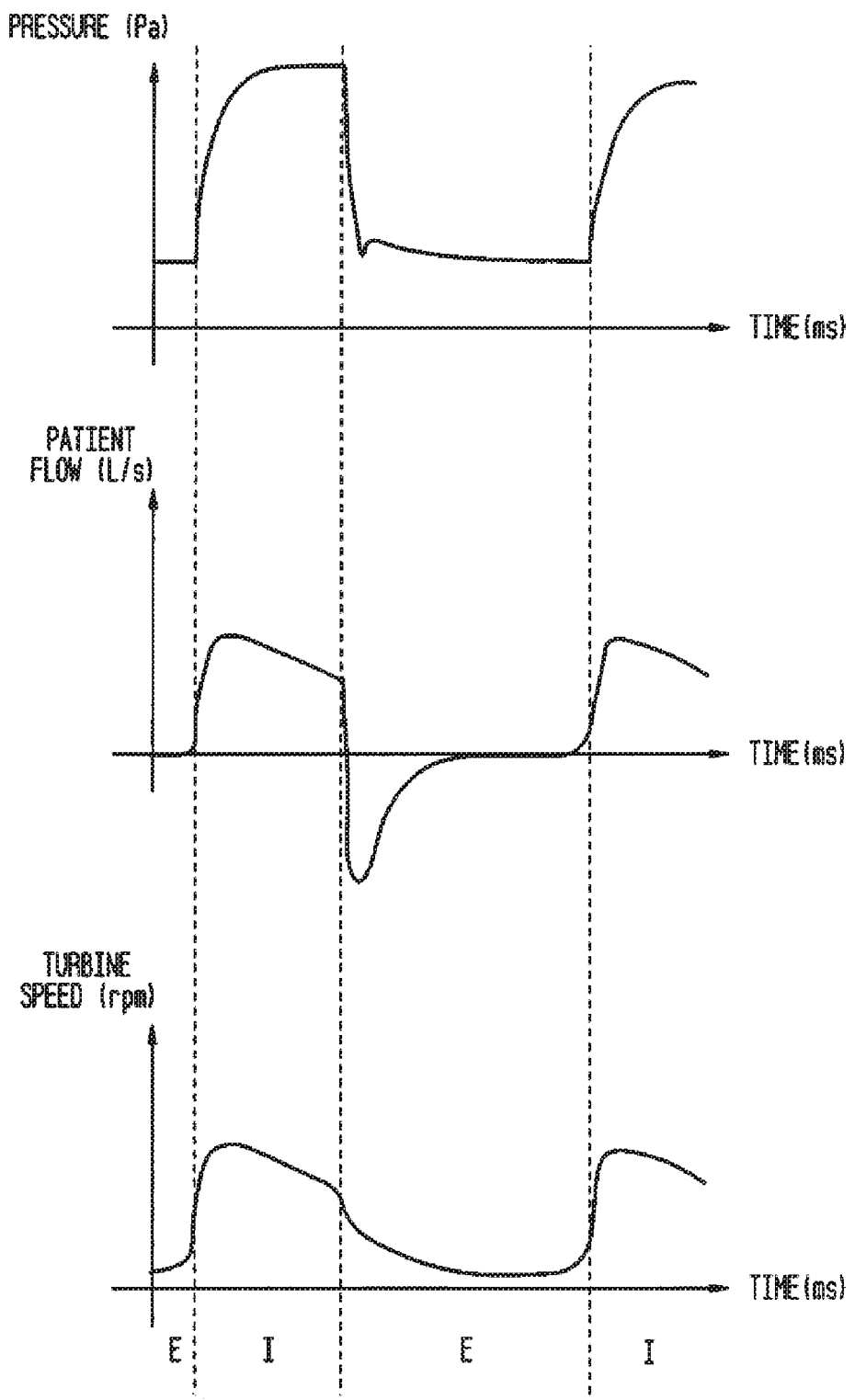

FIG. 4 includes three graphs showing a typical evolution of pressure, of flow, and of a parameter associated with the turbine of a device according to the invention, during an alternation of inspiratory and expiratory cycles.

FIGS. 5 to 8 illustrate four modes for detecting the start of a new inspiratory cycle, FIG. 9 illustrates a mode for detecting the start of a new expiratory cycle.

Figure 2:
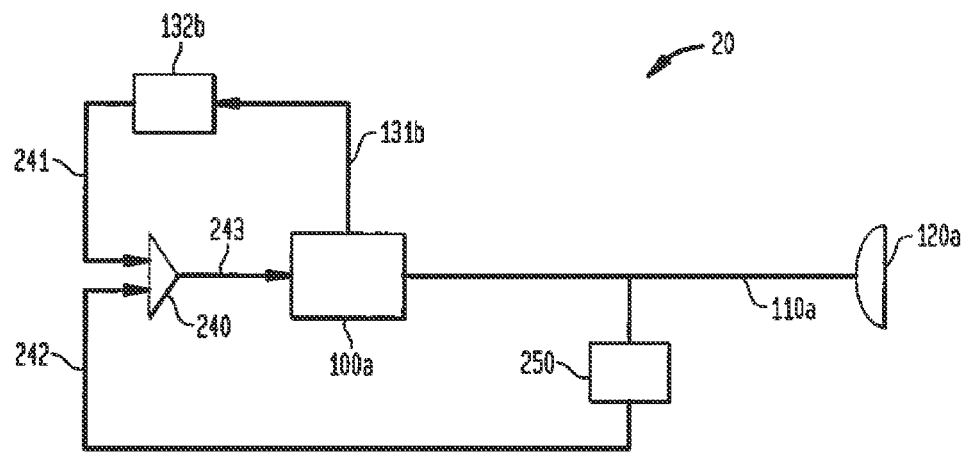
FIG. 2 is a schematic representation of a device according to the invention.

With reference now to FIG. 2, a device 20 according to the invention is shown in a schematic manner.

This device includes (as the devices of the state of the art) a turbine 100a, means 120a allowing a patient to receive the pressurized gas coming from the turbine, and a duct 110a for a carrying said gas from the turbine 100a to the means 120a.

Here again, the means 120a can be a mask comprising leakage means, or include an expiratory valve.

Figure 1A:
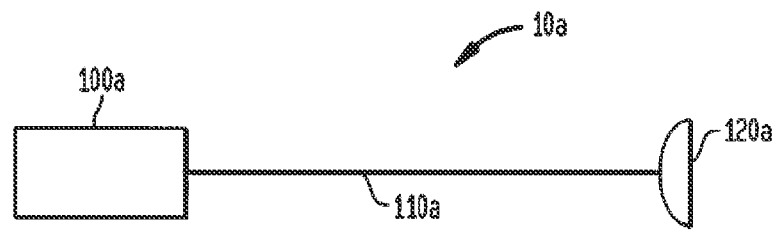
Figure 1B:
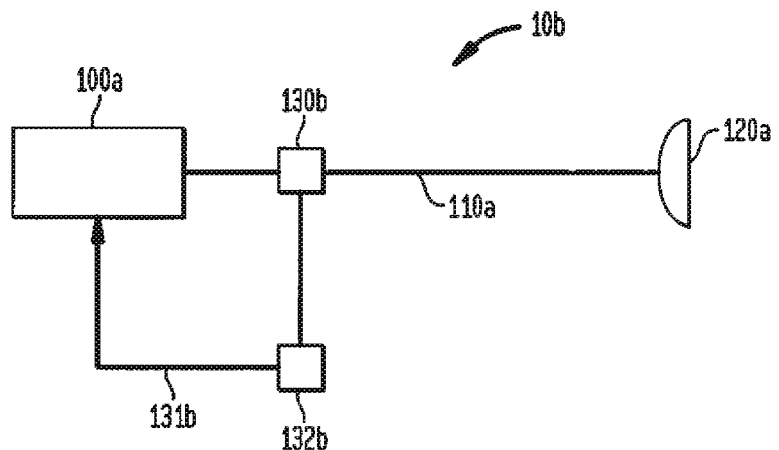

The device according to the invention includes (as the device shown in FIG. 1b) means for regulating the pressure.

Note however that in the case of the invention no flowmeter is associated to duct 210.

Means for regulating the pressure indeed include means of calculation 132b capable of receiving from the turbine a value of a signal which is characteristic of the operation of said turbine, via a connection 131b.

Means of calculation 132b include a microprocessor and are connected to a memory, in which different parameters are memorized.

The value characteristic of the operation of the turbine is a signal corresponding to the rotation speed of a rotating element of the turbine (e.g. its rotor).

In the remainder of this text, the signal received from the turbine will be called "measured speed".

To provide the means of calculation 132b with this measured speed, a speed sensor is integrated into the turbine. This speed sensor can be for example a Hall effect sensor.

Details will be provided hereafter concerning the different modes according to which the means of calculation are capable of automatically detecting the start of inspiratory and/or expiratory cycles, according to the signal received from the turbine and to different memorised parameters.

Means of calculation 132b are also connected to a circuit 240 for regulating the rotation speed of the turbine.

This circuit 240 receives two inputs:

Via a first connection 241, it receives a pressure setting elaborated by the means of calculation 132b, Via a second connection 242, it receives a pressure measured by a pressure sensor 250 on duct 110a.

As a function of these two inputs, the circuit 240 is capable of elaborating a rotation speed setting that is sends to turbine 100a via a connection 243.

This rotation speed setting is elaborated by the circuit 240 so that the pressure measured by sensor 250 reaches the value of the pressure setting received from the means of calculation 132b.

Note that the circuit 240 can be embodied by one or more component(s) of the turbine.

The device described above makes is possible to control the pressure of the respiratory gas carried by duct 110a to the patient.

More precisely, a first advantage of this control is to allow the establishment of a pressure with a desired value, corresponding to a value of the pressure setting that is received from means of calculation 132b.

In this way, when a bearing for which a constant pressure is to be maintained, circuit 240 is permanently active since it receives in real time the pressure measured by sensor 250, and it constantly adapts the rotation speed setting sent to the turbine in order to regulate the pressure.

And beyond this regulation of turbine rotation speed in order to maintain pressure at a given value, the invention makes it possible to detect in real time modifications in the respiratory behaviour of the patient, in order to trigger new inspiratory or respiratory cycles by having a modified pressure setting sent to the regulation circuit 240 by means of calculation 132b.

To this effect, means of calculation 132b use the measured speed received from the turbine.

This speed is constantly measured, and acquired at regular intervals, for example every 100 milliseconds. It is also possible to provide for continuous acquisition.

Note that in order to realise such a directing of the pressure setting according to a measured speed coming from the turbine, it is necessary that the sum of the inertia of the device remains low enough to be compatible with a control of this pressure setting in real time.

It would in fact not be acceptable for the new pressure setting to arrive at circuit 240 while the respiratory event that led to this new setting has occurred for a time that is too long.

In practice, the maximum acceptable delay between the respiratory event and the elaboration of the corresponding new pressure setting is about 50 to 100 milliseconds.

The inertia of the device which are likely to introduce delays in the elaboration of this pressure setting are mainly derived from:

turbine 100a duct 110a pressure sensor 250.

The inertia associated to duct 110a and to sensor 250 are classical pneumatic inertia, which are generally totally compatible with the maximum reaction timeframe mentioned above.

The inertia associated to the turbine must, as far as it is concerned, have a reduced value.

To this effect, a turbine with very low inertia has to be implemented in the invention.

Such a turbine can comprise e.g.:

a portion bearing the blades having a diameter of about 44 mm for a weight of about 5.6 g—which corresponds to an inertia of about 90 g·cm$^2$, a rotor having also an inertia of the same order (about 90 g·cm$^2$).

Therefore, the total inertia of the turbine remains lower than a value of about 200 g·cm$^2$.

Below are the general principles that are the basis for exploiting a measured speed here from the turbine in order to direct the pressure setting of the device.

Assuming that a patient who wants to breathe provides an energy
E which is equal to DxP, with:
D: instantaneous flow of the patient,
P: instantaneous pressure of the patient, The effort provided by the patient during an interval of time dt is the following:

$$dE/dt=(dD/dt)\cdot(dP/dt).$$

Since the device must compensate for the efforts of the patient, the turbine of the device must provide over the same time interval a work that corresponds to the effort of the patient.

The turbine of the device has a pneumatic power, which is according to the rotation speed of this turbine:

$$P_{turb}=f(n)$$

where $P_{turb}$: pneumatic power of the turbine and
f(n): function of turbine speed.

And the pneumatic energy of the turbine is therefore of the form:

$$E=dP_{turb}/dt=f'(n)$$

where
E: pneumatic energy,
$dP_{turb}/dt$: variation in pressure over interval dt,
f'(n): in relation to time of the function of the turbine speed.

The following balance must therefore be obtained:

$$De/dt=df'(n)/dt=d^2f(n)dt^2=dD/dt.dP/dt.$$

Thus is obtained:

$$dE/dt=f''(n)=dD.dP/dt^2$$

where dE: pneumatic effort,
f''(n): function of turbine speed resulting from f(n),
dD: variation in patient flow,
dP: variation in patient pressure.

Figure 3:
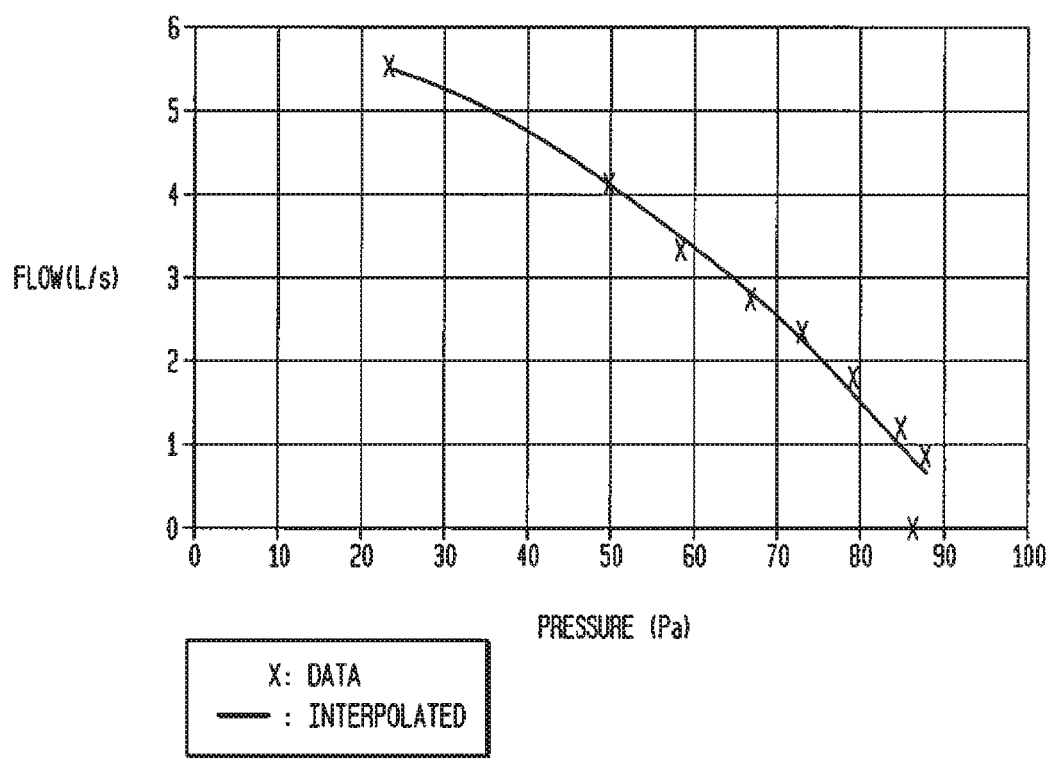
FIG. 3 is a graphical characteristic of a turbine implemented in a device according to the invention, showing for a given value of turbine rotation speed the relation between the pressure output of the turbine, and the flow generated by this turbine.

FIG. 3 shows a graph characteristic of a turbine implemented in a device according to the invention.

This graph shows the relationship between the flow and the pressure of the turbine, for a given rotation speed.

It is thus possible to plot such a characteristic curve for each rotation speed.

It is also possible to exploit the measurements of variation in turbine rotation speed, in order to determine, from a reference curve such as that in FIG. 3 and calculated for a given rotation speed, the characteristic parameters of the turbine for a second rotation speed.

The Applicant has thus determined a law for a reference rotation speed no (corresponding in the case of the turbine used to 46000 rpm).

For this rotation speed, between the flow and the pressure, a relationship is obtained of the following type:

$$Q=A2.Dp^2+A1.Dp+A0 \text{ with:}$$

$Dp$=pressure from sensor 250

$A2=-6.47.10^{-4}$ $A1=-3.45.10^{-3}$ $A0=-5.92$

This reference equation corresponds to the graph in FIG. 3.

For a second rotation speed n1 that is not equal to n0, the Applicant has established a law of transposition:

$T = Dp \cdot n0/n1^2$ and $Q = (A2 T2 + A1 t + A0) \cdot n1/n0$, with:

$Dp$=pressure from the sensor, $T$=rotation speed adaptation factor, $Q$=flow,

This law of transposition establishes a correspondence between the turbine rotation speed and the flow parameters of the respiratory gas generated by this turbine.

It makes it possible to determine the conditions for establishing respiratory gas flow, and to control the operation of the device, by using a measurement of turbine rotation speed.

Note that in the case of the invention, a measurement of flow is not exploited, but rather a measurement of turbine rotation speed.

This gives access in particular to the following advantages:
to be free from the presence of a flowmeter,
to work in real time in relation to the operation of the operation (indeed, in known devices in which the control is performed using a flow measurement, a certain time is needed for a modification in the turbine operating conditions translate into a difference in flow at the level of the flowmeter—and this "certain time" is largely greater than the limits mentioned above, making a "real time" control impossible).

It is specified regarding this aspect that the device and process according to the invention use only a measurement of speed of the turbine.

In this respect, the invention totally differs from known devices such as the one described in patent EP 656 216.

This patent mentions turbine motor speed as a parameter which can be used in some way to control the operation of the device.

This patent further states that modifications of the airflow which are due to the respiration of the patient will alter parameters such as the turbine motor's speed and/or current.

It further explains that it proposes to use specific signals to detect the points at which the patient starts to inhale and exhale.

As exposed column 3 lines 37-39 of this patent, these specific signals can be derived:
Either from the motor speed and power measurements (first option), or
From the spill valve position and power measurements (second option).

In the first option, motor speed is thus used in some way for detecting the beginning/end of respiratory cycles. But it is to be noted that motor speed is in no way used by itself, as a single control parameter. This parameter is indeed systematically used in combination with power measurements.

This is understandable, since turbines known at the priority date of EP 656 216 had quite an important inertia—in the order of 1500 g·cm² at least.

For such turbines, a change in the airflow conditions would not change turbine speed before some inertia time (greater than the limit mentioned above).

Thus, in order to detect such airflow changes in "real time" (or at least as fast as possible, which is of course desired), the mere monitoring and exploitation of turbine speed would in any event not have been appropriate.

Therefore, such known devices have to use as a main parameter not turbine speed but motor power, in order to detect airflow changes as fast as possible.

In turbines such as the ones known at the priority date of this patent, this parameter "motor power" will indeed vary much faster than the turbine speed, which can change only after some time because of the large inertia of the turbine.

It should be further noted that the systematic exploitation of motor power in the case of EP 656 216 makes it necessary to filter the signals based on power.

This is not the case for the present invention, turbine speed in itself requires no filtering, and can be exploited per se.

The invention also strongly differs from earlier disclosures such as the one of EP 505 232, which discloses the use of a signal which is the control signal sent to the turbine itself.

The idea which is exploited in this document is the fact that when airflow conditions change, the control loop which sends said control signal to the turbine will adapt very quickly its control signal in reaction to the change in pressure detected in the inspiration duct.

Thus, this other prior art patent does not teach or even suggest using directly the turbine speed to detect new respiratory cycles and control the operation of the turbine.

Furthermore, here again, the signal used for controlling the turbine does not provide a direct indication of the airflow conditions: the signal indeed comprises electrical noise which must be filtered.

And in any event, here again at the priority date of the patent the turbines used in respiratory devices had a large inertia which made the device incompatible with a real time control of the turbine based on turbine speed measurements.

Finally, it is specified that the prior art discloses in US 2003/0015200 a respiratory devices which use a speed signal for its operation.

This document indeed mentions a use of turbine speed.

But the use disclosed by this document is very different from the use made in the present invention: this prior art document concerns a very specific device with two gas sources (a pressurized gas source, and a depressurized source).

The general architecture of the device of this document is thus completely different from the architecture of the device of the present invention, which comprises only one source for the respiratory gas.

And not surprisingly, this fundamental difference in the structure of the device is also associated with a difference in the exploitation of the turbine speed: in the case of US 2003/0015200 turbine speed is used for activating a three-way valve 211, not for controlling a turbine.

In fact, US 2003/0015200 is not concerned by the control of a turbine.

In the case of this document the control of the airflow conditions is indeed sought through this valve 211, which selectively connects the patient to one of the two gas sources 234, 236.

As said above, the device according to the invention is capable of elaborating in real time (i.e. with a timeframe less than the maximum timeframe mentioned above) pressure settings corresponding to new inspiratory and/or expiratory cycles.

More precisely, means of calculation 230 are associated with several programs for detecting inspiratory cycles being able to operate simultaneously.

Each one of these programs for detecting inspiratory cycles follows in real time the changes in certain parameters of the respiratory activity of the patient, and is capable of triggering a new inspiratory cycle when conditions that are proper to the program are met.

And when the different programs operate simultaneously, as soon as the conditions corresponding to a new inspiratory cycle for one of the programs are met, the means of calculation 230 elaborate a pressure setting corresponding to a new inspiratory cycle and transmit this pressure setting to the turbine.

Below is described the different detection modes for a new inspiratory cycle, corresponding to these different programs.

Note that it is possible to implement only one of these programs, or to only implement certain ones simultaneously.

It is also possible to implement them all simultaneously as mentioned above.

Before describing in greater detail the different detection modes for a new inspiratory cycle, in reference to FIG. 4 the typical change in several parameters during a succession of inspiratory and expiratory cycles is reminded.

The two curves in the upper portion of this figure show respectively the change in the pressure in the duct carrying the respirator gas and in the corresponding gas flow.

The different cycles are marked in the lower portion of the figure (I for the inspiratory cycle, E for the expiratory cycle).

The lower curve shows the change during the same succession of cycles in the turbine speed signal.

Note that this curve varies according to the turbines used, the curve shown in FIG. 4 (and which will be used in the rest of this text) corresponding to a turbine of which the inertia corresponds to the values mentioned above.

The lower curve shows the fact that turbine rotation speed in the device is notconstant.

On the contrary, this speed is higher during the inspiratory phases, and lower during the expiratory phases.

Therefore, the change in this rotation speed as a function of time contains information associated to the respiratory behaviour of the patient.

And as we shall see, the invention uses this information to detect new inspiratory or expiratory cycles, and consequently modifiy the pressure setting which is elaborated by means of calculation 230, and send to the regulation circuit 240.

It is to be noted that in all the FIGS. 5 to 8, which show different modes for triggering inspiratory and/or expiratory cycles, the values measured in real time are represented with white points, while black points represent memorised values.

Figure 5:
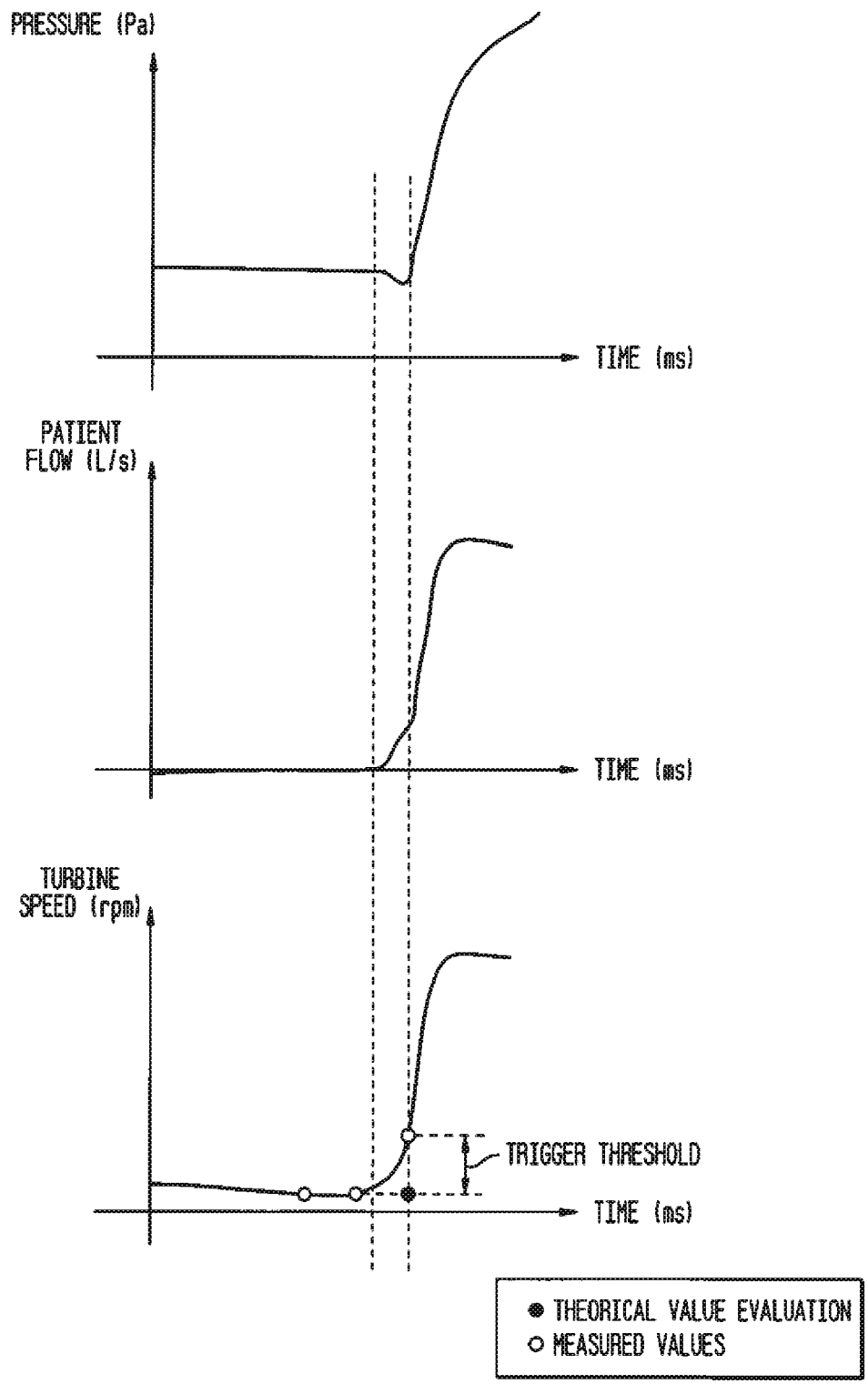

In reference now to FIG. 5 the triggering of an inspiratory cycle according to a first mode, called "fast effort detection", is described.

As we shall see, this detection mode uses a comparison between
- an instantaneous speed actually measured by the speed sensor of the turbine (it is reminded that in this text "speed" designates the rotation speed of a rotating element of the turbine—typically its rotor),
- and parameters memorised in the memory mentioned which has been above and which is associated to means of calculation 230.

More precisely, the variations in this rotation speed are used in the different modes for detecting the start of inspiratory cycles, but also in the detection of the start of expiratory cycles.

Returning to the description of this first mode for detecting the start of an inspiratory cycle, the program associated with this first mode constantly evaluates an extrapolation f the speed according to the latest measured speeds.

This extrapolation can for example be performed on the basis of the last two speeds actually measured.

The value extrapolated in this way is memorised in the memory associated to the means of calculation 230. It is represented by a black dot on the graph in FIG. 5.

At every given instant, an extrapolation is available that corresponds to an expected speed at the next speed measurement.

And during this next speed measurement, the program compares the extrapolated speed value with the value of speed actually measured.

If the difference between these two speed values is greater than a given threshold, the program concludes to an initiation of a new respiratory cycle.

In this case, means of calculation 230 consequently elaborate a new adapted pressure setting.

This threshold can be for example 2200 points, with "points" being a unit that is representative of the turbine rotation speed.

Note that this detection mode can—as with all the other modes for detecting the start of a new inspiratory cycle—be disabled for a given timeframe following the start of a new expiration (with expiratory cycles being initiated in the manner that will be described further on in this text).

An auto-triggering of the inspiratory cycle by error is therefore avoided in the case for example of an expiratory valve rebounding (which corresponds to a negative variation then a positive one for pressure at the start of expiration).

The timeframe for disabling this triggering of a new inspiratory cycle (i.e. the time during which the triggering is disabled) can be for example about 300 milliseconds.

FIG. 6 shows a second mode for detecting a new inspiratory cycle.

This mode is activated when operating stability in the turbine is observed for a duration that is greater than a given minimum value, said given value being memorised in the memory of the means of calculation 230 as all the operating parameters for the device.

Said given minimum value can be 300 milliseconds, for example.

Note that "stability" is defined as the operating conditions that correspond to speed variations contained within given percentages of variation (corresponding to a triggering threshold).

By way of example, for a nominal turbine rotation speed of about 40,000 to 6,0000 rpm, these given variation percentages correspond to values of about 100 to 400 rpm, depending on the pressure present in duct 210.

Note that the lower this pressure is, the more it is possible to tolerate large variations in speed, while still considering that the state is "stable".

Thus, in a range of low pressures, the range of speed variations corresponding to "stable" operating conditions is enlarged, and approaches a maximum range of 400 rev/min more or less.

When this mode is in this way activated, the average value of rotation speed corresponding to the range of stability is memorised in the memory associated to the means of calculation 230.

Since turbine rotation speed is always measured in real time, a new inspiratory cycle is triggered by the means of calculation when the absolute value of the difference between the measured speed and said memorised stability value is greater than the triggering threshold.

This triggering threshold can be for example 1800 points. We have seen that its value can further depend on the pressure measured FIG. 6 thus corresponds to triggering an inspiratory cycle in a mode called "detection of substantial effort after stability".

FIG. 7 corresponds to a similar mode, operating on the basis of different values.

In this case, the mode is called "detection of substantial effort after prolonged stability".

In this case, the duration of stability from which the value of speed is memorised is 500 milliseconds, not 300 milliseconds. It is in any event longer than the corresponding value for the preceding mode.

And the triggering threshold is lower (typically 1500 points, instead of 1800).

FIG. 8 shows another mode for triggering an inspiratory cycle, called "cycle to cycle detection of effort".

This mode is implemented by memorising the value of measured rotation speed at the end of the previous expiratory cycle.

This memorised value in association with means of calculation 230 will serve as a reference for triggering not the inspiratory cycle that immediately follows the acquisition of this memorised value, but of the inspiratory cycle that will follow yet.

The program corresponding to this mode triggers a new inspiratory cycle when the absolute value of the difference between the measured speed value and this memorised value is greater than a given triggering threshold.

This triggering threshold can be for example about 2200 to 2500 points (note that the curves are not strictly to scale—in particular with regards to the triggering thresholds).

In reference now to FIG. 9, a mode for triggering expiratory cycles is shown.

To implement this triggering, the device memorises the maximum value for turbine rotation speed (this maximum is produced during inspiratory cycles).

A new maximum can therefore be memorised at each inspiratory cycle.

It is also possible to only memorise a new maximum value only every N inspiratory cycles, N being able to be set freely.

When the speed measured in real time goes down to a value that represents a determined proportion of this maximum, means of calculation 230 provoke the triggering of a new expiratory cycle, and elaborate to this effect an adapted pressure setting.

The proportion in question can be for example 70% of the memorised maximum.

Note that this triggering of a new expiratory cycle can be disabled for a given duration (for example 200 milliseconds) after the occurrence of the maximum rotation speed in the inspiratory cycle.

It thus appears that the invention makes it possible to regulate in real time the operation of a turbine, by following the rotation speed of this turbine and the pressure of the gas carried to the patient.

And the invention also makes possible, using the monitoring of the turbine rotation speed, to trigger new inspiratory and/or expiratory cycles, by modifying a pressure setting sent to the turbine.

It is to be noted that the invention makes it possible to avoid using a flowmeter, and the limitations that are associated with such a component.

And as mentioned above, this invention also makes it possible to actually control the device in real time, which improves patient comfort.

The invention claimed is:

1. A breathing assistance device, comprising:
a turbine to generate a flow of pressurised respiratory gas, said turbine having an inertia less than about 200 g·cm$^2$,
a duct adapted to carry the pressurised gas to a patient, and
control means for controlling gas pressure capable of computing a pressure setting for the turbine,
wherein the turbine is connected to a speed sensor capable of acquiring a signal corresponding to a rotation speed of a rotating element of the turbine, and the control means includes means of calculation connected to said speed sensor to compute the pressure setting using only said speed signal and send the pressure setting to the turbine, said means of calculation being adapted to detect new inspiratory or expiratory cycles using only said speed signal, and consequently adapting a level of said pressure setting.

2. A device as claimed in claim 1, wherein said speed sensor implements a Hall effect sensor.

3. A device as claimed in claim 1, wherein said speed sensor is a sensor capable of acquiring a turbine speed signal directly connected to the rotation speed of the rotating element of the turbine.

4. A device as claimed in claim 1, wherein the means of calculation computes the pressure setting according to variations in speed.

5. A device as claimed in claim 1, further comprising a program for detecting an inspiratory cycle using a comparison between:
a speed value stored in a memory of the device, said speed value being extrapolated using recent values of measured speeds, and an actually measured instantaneous speed.

6. A device as claimed in claim 1, further comprising a program for detecting an inspiratory cycle using a comparison between:
a speed value stored in a memory of the device, said speed value being representative of a recent speed bearing, and
an actually measured instantaneous speed.

7. A device as claimed in claim 5, further comprising a program for detecting an inspiratory cycle using a comparison between:
a speed value stored in a memory of the device, said speed value being representative of a speed at an end of an expiratory cycle, and
an actually measured instantaneous speed.

8. A device as claimed in claim 5, further comprising several programs for detecting an inspiratory cycle operating simultaneously, and is capable of computing a pressure setting corresponding to a start of inspiratory cycle as soon as one of said programs for detecting the inspiratory cycle has signalled a start of inspiration.

9. A device as claimed in claim 5, wherein the program for detecting the inspiratory cycle is configured to be disabled for a determined duration following a start of a new expiratory cycle.

10. A device as claimed in claim 1, further comprising a program for detecting an expiratory cycle.

11. A device as claimed in claim 10, wherein said program for detecting the expiratory cycle uses a comparison between:
a maximum turbine speed stored in a memory of the device and corresponding to an inspiratory cycle, and
an actually measured instantaneous speed.

12. A device as claimed in claim 1, wherein said means of calculation includes a microprocessor connected to the speed sensor and to a turbine pressure setting input.

13. A device as claimed in claim 1, wherein the device further includes a pressure-regulating loop comprising:
   a pressure sensor on the duct, and
   a circuit receiving the pressure setting coming from the means of calculation as well as a pressure measured by the pressure sensor, said circuit being capable of computing an instantaneous rotation speed setting for the turbine, said circuit being connected to a turbine speed setting input.

14. A method for regulating a pressure of a respiratory gas delivered by a turbine to a patient, the method comprising:
   providing, with a speed sensor, a signal representative of a rotation speed of a rotating element of the turbine, said turbine having an inertia less than about 200 g·cm$^2$; and
   computing, with a processor, a pressure setting for the turbine based only on the signal representative of the rotation speed,
   said method being adapted to detect new inspiratory or expiratory cycles using only said signal, and of consequently adapting a level of the pressure setting with the processor.

15. A method as claimed in claim 14, wherein said signal corresponds to the rotation speed of the turbine rotor.

16. A method as claimed in claim 14, wherein the method implements a program for detecting an inspiratory cycle using a comparison between:
   a speed value stored in a memory, said speed value being extrapolated from recent values of measured speeds, and
   an actually measured instantaneous speed.

17. A method as claimed in claim 14, wherein the method implements a program for detecting an inspiratory cycle using a comparison between:
   a speed value stored in a memory, said speed value being representative of a recent speed bearing, and
   an actually measured instantaneous speed.

18. A method as claimed in claim 14, wherein the method implements a program for detecting inspiratory cycles using a comparison between:
   a speed value stored in a memory, said speed value being representative of a speed at the end of an expiratory cycle, and
   an actually measured instantaneous speed.

19. A method as claimed in claim 16, wherein the method implements several programs for detecting inspiratory cycles operating simultaneously, and computes the pressure setting corresponding to an inspiratory flow as soon as one of said programs for detecting the inspiratory cycles has signalled the start of inspiration.

20. A method as claimed in claim 16, wherein the program for detecting inspiratory cycles is disabled during a determined duration following the start of a new expiratory cycle.

21. A method as claimed in claim 14, wherein the method implements a program for detecting expiratory cycles.

22. A method as claimed in claim 21, wherein said program for detecting expiratory cycle uses a comparison between:
   a maximum turbine speed stored in a memory and corresponding to an inspiratory cycle, and
   an actually measured instantaneous speed.

* * * * *

UNITED STATES PATENT AND TRADEMARK OFFICE
CERTIFICATE OF CORRECTION

PATENT NO. : 8,251,062 B2
APPLICATION NO. : 10/553643
DATED : August 28, 2012
INVENTOR(S) : Chalvignac Page 1 of 1

It is certified that error appears in the above-identified patent and that said Letters Patent is hereby corrected as shown below:

In the Specification

Column 1, line 34, "is" should read -- are --.
Column 4, line 31, "a carrying" should read -- carrying --.
Column 4, line 66, "sends" should read -- sent --.
Column 5, line 7, "is" should read -- it --.
Column 5, line 53, "timeframe" should read -- time frame --.
Column 8, line 34, after "2003/0015200" delete "a".
Column 9, line 32, "notconstant" should read -- not constant --.
Column 9, line 64, "f" should read -- of --.
Column 10, line 21, "timeframe" should read -- time frame --.
Column 10, line 28, "timeframe" should read -- time frame --.
Column 10, line 67, at end of sentence insert -- . --.
Column 11, line 24, delete "yet".

In the Claims

Column 12, line 51, Claim 8, after "start of" insert -- an --.
Column 14, line 26, Claim 22, after "detecting" insert -- an --.

Signed and Sealed this
Seventh Day of January, 2014

Margaret A. Focarino
*Commissioner for Patents of the United States Patent and Trademark Office*